United States Patent [19]

Whitlock et al.

[11] Patent Number: 5,859,277
[45] Date of Patent: Jan. 12, 1999

[54] SILICON-CONTAINING SOLID SUPPORT LINKER

[75] Inventors: Howard W. Whitlock; Karin Kay Maxson, both of Madison, Wis.

[73] Assignee: Wisconsin Alumni Research Foundation, Madison, Wis.

[21] Appl. No.: 882,183

[22] Filed: Jun. 25, 1997

[51] Int. Cl.$^6$ ........................................................ C07F 7/08
[52] U.S. Cl. ................ 556/400; 556/418; 556/489; 556/465; 526/279; 526/296; 526/336; 526/346; 526/342; 526/347.1; 526/347.2; 585/469; 585/601; 585/733
[58] Field of Search ..................... 556/487, 489, 556/465, 400; 526/279, 296, 336, 346, 347, 347.1, 347.2; 585/469, 601, 733

[56] References Cited

U.S. PATENT DOCUMENTS

| | | | |
|---|---|---|---|
| 4,230,815 | 10/1980 | Itoh et al. | 556/487 X |
| 4,694,092 | 9/1987 | Takahata et al. | 556/400 |
| 4,824,950 | 4/1989 | Barcza | 556/400 X |
| 4,894,468 | 1/1990 | Wilchek et al. | 556/400 X |
| 5,374,755 | 12/1994 | Neue et al. | 556/400 |
| 5,576,453 | 11/1996 | Buese | 556/400 |

OTHER PUBLICATIONS

"A Silicon–Based Linker for Traceless Solid–Phase Synthesis," Matthew J. Plunkett and Jonathan A. Ellman, Department of Chemistry, University of California, *J. Org. Chem.* 1995, 60, 6006–6007.

"Bromination and Lithiation: Two Important Steps in the Functionalization of Polystyrene Resins," M. Jean Farrall and Jean M.J. Fréchet, Dept. of Chemistry, University of Ottawa, *J. Org. Chem.*, vol. 41, No. 24, 1976, 3877–3882.

"Polymer–anchored Organosilyl Protecting Group in Organic Synthesis," Tak–Hang Chan and Wen–Qiang Huang, Dept. of Chemistry, McGill Univ., *J. Chem. Soc., Chem. Commun.*, 1985, 909–911.

"Synthesis and Applications of Small Molecule Libraries," Lorin A. Thompson and Jonathan A. Ellman, Dept. of Chemistry, Univ. of Calif., *Chem. Rev. 1996*, vol. 96 No. 1, 555–600.

*Primary Examiner*—Paul F. Shaver
*Attorney, Agent, or Firm*—Lathrop & Clark

[57] ABSTRACT

A compound of the formula

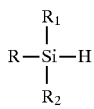

where R is a solid support; $R_1$ and $R_2$ are alkyl, unsubstituted alkyl, or phenyl, and where $R_1$ and $R_2$ can be the same or different, for use in solid-phase synthesis.

21 Claims, No Drawings

SILICON-CONTAINING SOLID SUPPORT LINKER

FIELD OF THE INVENTION

The present invention relates to linkers for solid-phase synthesis, and more particularly relates to a silicon-based linker for solid-phase synthesis.

BACKGROUND OF THE INVENTION

In the search for therapeutic agents, one of the first steps is to identify specific compounds that bind to the receptor or enzyme target of interest. Once these compounds are identified, numerous analogs or related compounds are synthesized and evaluated for maximum pharmacological activity. Due to the need to synthesize and evaluate large numbers of compounds in an efficient manner, methods have been developed for the generation of large combinatorial libraries of compounds. The first combinatorial libraries generated were those containing peptides and oligonucleotides. However, these compounds generally have poor oral activity and rapid in vivo clearance. Therefore, the utility of these compounds as therapeutic agents is often limited.

Unlike the peptides and oligonucleotides, many small organic compounds, i.e., those with a molecular weight less than 700, have favorable pharmacodynamic and pharmacokinetic properties. Thus, the design, synthesis and evaluation of libraries comprising small organic molecules is at present of major interest in the field of organic chemistry.

Most of the organic chemical libraries generated to date are made using solid-phase synthesis methods. In solid-phase synthesis, the compounds of interest are made on a polymeric solid support material, such as cross-linked polystyrene. There are general advantages to such solid-phase synthesis. First, isolation of the support-bound reaction products is achieved by washing away reagents from the support-bound material, and therefore reactions can be driven to completion by the use of excess reagents. Second, methods are available for the manipulation of discrete compounds and for tracking the identity of compounds when compounds are attached to a solid support. Also, desired products can be easily isolated without the use of expensive chromatographic methods.

In solid-phase synthesis, the compounds of interest are generated while attached to the solid support via a linkage element, or "linker." Ideally, the linker should be stable to all reactions used in a synthesis sequence and should be cleaved quantitatively under conditions that do not degrade the desired target compounds.

Linkage strategies are generally grouped into four categories. The first is to link through functionality already present in the desired target compounds, as is done in peptide and oligonucleotide synthesis. The second strategy is a cyclative cleavage whereby the linker is incorporated into the final compound. In many cases, however, these two strategies cannot be used with a desired class of compounds or these strategies limit the chemistry that can be performed. Therefore, the third and more general strategy is to introduce an auxiliary functional group, such a phenol, amide, or carboxylate, as a handle for the linker attachment. After cleavage from the solid support when synthesis is complete, this functional group can have a negligible, positive, or negative effect on the biological or chemical activity of the target compounds, depending on the location of the functional group. Thus, this approach introduces an undesirable degree of unpredictability to the synthesis.

An alternative fourth approach is to use a linker that can be removed efficiently and quantitatively when desired, leaving behind no trace of the solid-phase synthesis. One such linker is a silicon-based linker, from which the compounds of interest can be separated by protodesilation, to leave no trace of the linkage site. Various silicon-based linkers have been disclosed in the literature. In *J. Org. Chem.*, 1976, 41, 3877, a dimethylchlorosilane linker is disclosed. This linker is anchored to a solid support, such as a styrene-divinylbenzene copolymer. However, the synthesis scheme disclosed to generate this polymer-anchored linker has not been found to be reproducible. Moreover, the linker is not stable under standard storage conditions, because the silyl chloride is highly susceptible to hydrolysis.

A diphenylchlorosilane linker is disclosed in *J. Chem. Soc.*, Chem. Commun., 1985, 909. Again, this linker is attached to a styrene-divinylbenzene copolymer. Due to the presence of the chloro group, this linker suffers from the same stability problems as the linker discussed above. In *J. Org. Chem.*, 1995, 60, 6006 a silyl-substituted (aminoaryl) stannane ester derivative linker is disclosed. However, synthesis of this linker is complicated and requires that the linker be separately produced before it is joined to the solid support.

Accordingly, a need exists for a solid support linker compound for use in solid-phase synthesis that is stable under storage conditions, but also that can easily be rendered highly reactive. A need also exists for a linker that can be easily produced on solid support. Further, a need exists for a solid support linker that can be readily isolated and purified in high yields. These needs are met by the silicon-based solid support linkers of the present invention.

SUMMARY OF THE INVENTION

The present invention provides compounds of the formula

where R is a solid support, $R_1$ and $R_2$ are alkyl, substituted alkyl, or phenyl, and where $R_1$ and $R_2$ can be the same or different.

The compounds of formula (I) are stable under normal storage conditions, and can be easily isolated and purified. Moreover, the compounds of formula (I) can readily be made highly reactive via lithiation, to form the silyl lithium species, after which both saturated and unsaturated halides can be attached to yield compounds of the formula

where R, $R_1$ and $R_2$ are as described above, and $R_3$ is alkyl, aromatic, or unsaturated alkyl, where $R_3$ can be substituted or unsubstituted.

Where $R_3$ is, for example, an unsaturated alkyl group, the compounds of formula (II) can undergo acid catalyzed cyclizations to generate ring systems while simultaneously cleaving from the silicon containing support at the silicon atom, to produce compounds free of the silicon-containing solid support, leaving no trace of the solid-phase reaction system. Therefore, the compounds of the present invention are extremely useful in easily and efficiently creating combinatorial libraries of small organic compounds.

DESCRIPTION OF THE PREFERRED EMBODIMENTS

As stated above, the present invention provides novel solid-support linker compounds for solid-phase synthesis having the formula

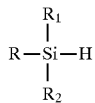

where R is a solid support, $R_1$ and $R_2$ are alkyl, substituted alkyl, or phenyl, and $R_1$ and $R_2$ can be the same or different.

The compounds of formula (I) above are prepared as follows. First, the solid support of choice is halogenated to yield a compound having the formula R-X, where R is the solid support and X is bromine or iodine. Bromine is preferred, due to its ease of preparation. The solid support can be chosen from any of those conventionally used in solid-phase synthesis, including solid supports comprising polystyrene. Suitable solid supports for use in the present invention include polystyrene, polystyrene/divinylbenzene copolymers, with 1%–2% divinylbenzene cross-linking, and polystyrene/polyethylene glycol copolymers. A polystyrene/divinylbenzene copolymer (2% cross-linking) is preferred, because it has good swelling properties in a variety of solvents.

The halogenated solid support is prepared by conventional means, such as those disclosed in *J. Org. Chem.*, 1976, 41, 3877, which is incorporated herein by reference. There, preparation of brominated solid support is accomplished using a thallic acetate catalyst.

The halogenated solid support is then reacted with an alkyl lithium compound, to produce a compound of the formula R-Li. In the preferred reaction sequence, the halogenated solid support is suspended in THF, and n-BuLi is added. Other preferred lithium-containing compounds that are useful in the present invention are phenyllithium and t-BuLi.

The compounds of formula (I) above can then be prepared in situ from the lithiated solid support. The lithiated solid support is suspended in THF, and a silane of the formula $HSiR_1R_2Cl$ is added, to produce the novel compounds of formula (I). As stated above, $R_1$ and $R_2$ are alkyl, substituted alkyl, or phenyl, where $R_1$ and $R_2$ can be the same or different. Preferably, $R_1$ and $R_2$ are both $C_{1-4}$ alkyl. Most preferably, both $R_1$ and $R_2$ are methyl, to avoid steric hindrance.

The compounds of formula (I) above are stable in air under normal storage conditions, thus allowing them to be easily stored for later use. Thus, the compounds of the present invention can be stored in air at a temperature from about 30° C. to about −20° C. without hydrolyzing or otherwise degrading.

As stated above, the novel solid-support linker compounds of formula (I) can then be used to form combinatorial libraries of small organic compounds. These small organic compounds are formed as follows. First, the compound of formula (I) is lithiated in THF at room temperature with a soluble form of lithium, such as lithium biphenylide, lithium nap alenide, or metallic lithium, in the presence of catalytic amounts of lithium biphenylide or lithium napthalenide to form he highly reactive silyl anion, which is then reacted with a compound of the formula $R_3CH_2Z$ where $R_3$ is alkyl, aromatic or unsaturated alkyl and can be substituted or unsubstituted, and Z is a leaving group. Preferably, Z is bromine or chlorine, with chlorine being most preferred. $R_3$ is preferably unsaturated alkyl; for example, the group $R_3CH_2$ can include allyl, dimethylallyl, or geranyl.

Where $R_3$ is unsaturated alkyl, the $R_3$ group on the compounds of formula (II) can then, if desired, be cyclized via a cation-pi cyclization to afford a bicyclic system. Cleavage from the silane-based solid support can then easily be accomplished by the use of fluoride ions, such as HF or TBAF, or by generalized electrophilic attack, resulting in the compounds of interest.

The preparation of the novel compounds of the present invention is illustrated in the following Examples.

EXAMPLE 1

Preparation of Poly(bromo)styrene

A polystyrene/divinylbenzene copolymer (2% cross-linking), was brominated according to the method disclosed in *J. Org. Chem.*, 1976, 41, 3877. The resin (5g) was swelled in 75 mL of CCl4 in a 100 mL round bottom flask. Thallium acetate sesquihydrate (300 mg) was added, and the flask was vortexed for 25 minutes at room temperature. Bromine (3.4g) was dissolved in 5 mL of $CCl_4$, and added to the reaction flask, which then was heated in an oil bath at 80° C. overnight. The reaction was cooled to room temperature, and the pale orange resin was collected by filtration, washed with acetone, methanol, benzene, and $CCl_4$, and dried. The resin was analyzed by gel-phase Carbon-13 NMR, and determined to be poly(bromo)styrene.

EXAMPLE 2

Preparation of poly(dimethylsilyl)styrene

The resin of Example 1 (300 mg, 0.44 mmol) was swelled in dry THF (4 mL) under $N_2$ flow. The resin was cooled to −78° C. and n-BuLi (528 uL of 2.5 M in hexanes, 0.88 mmol) was added. The resin immediately turned brown/orange and after 5 minutes, excess n-BuLi was removed by washing with cold THF. Chlorodimethylsilane (293 uL, 1.76 mmol) was added, causing the resin to turn pale orange. The reaction was allowed to warm to 25° C. The resin was washed with THF, water, methanol, and $CHCl_3$, and dried. The resin was analyzed by gel-phase Carbon-13 NMR and determined to be poly(dimethylsilyl)styrene.

EXAMPLE 3

Preparation of poly(benzyldimethylsilyl)styrene

The resin of Example 2 (125 mg) and lithium wire (99.9%), which was cut into small pieces and washed with hexanes, were suspended in 5 mL of THF in a round-bottomed flask, and a small amount of napthalene (15 mg) was added. The solution turned black and was stirred at room temperature overnight. The lithium metal was then removed, and the flask was cooled to 0° C., whereupon 95 uL of a benzyl chloride solution enriched with 10% Carbon-13 labeled benzyl chloride in 5 mL of THF was added to the resin. The resin was stirred at 0° C. for two hours, and then warmed to room temperature and stirred for four more hours. The resin slowly turned orange. The resin was quenched. It was filtered and washed successfully with $NH_4Cl$, water, THF and $CHCl_3$. The resin turned orange/brown upon addition of the $NH_4Cl$. The resin was dried overnight and was then analyzed by gel-phase Carbon-13 NMR. The resin was identified as poly(benzyldimethylsilyl) styrene, in a yield of 65%.

EXAMPLE 4

Preparation of poly(dimethylallyldimethylsilyl)styrene

The procedure of Example 3 was repeated, with a dimethylallyl chloride solution enriched with 10% Carbon-13 labeled dimethylallylchloride replacing the benzyl chloride solution of Example 3. Analysis of the resulting resin by gel-phase Carbon-1 3 NMR revealed the resin to be poly(dimethylallyidimethylsilyl)styrene, in a yield of 42%.

EXAMPLE 5

Preparation of poly(geranyidimethylsilyl)styrene

The procedure of Example 3 was repeated, with a geranyl chloride solution enriched with 10% Carbon-13 labeled geranyl chloride replacing the benzyl chloride solution of Example 3. Analysis of the resulting resin by gel-phase Carbon-13 NMR revealed the resin to be poly(geranyldimethylsilyl)styrene, in a yield of 78%.

EXAMPLE 6

Preparation of poly(octyldimethylsilyl)styrene

The procedure of Example 3 was repeated, with an octyl chloride solution enriched with 10% Carbon-13 labeled octyl chloride replacing the benzyl chloride solution of Example 3. Analysis of the resulting resin by gel-phase Carbon-13 NMR revealed the resin to be poly(octyidimethylsilyl)styrene, in a yield of 76%.

EXAMPLE 7

Preparation of 2,6, 7-trimethyl-2,6-octadiene

Poly(geranyidimethylsilyl)styrene prepared in accordance with Example 5 was suspended in 600 uL of 1 M TBAF in THF in a glass tube. The tube was sealed and the reaction was heated to 95° C. for 4 hours. The solid support was removed via filtration and the solvent was analyzed by GC/MS to yield one product. The yield of the reaction was determined to be 15% using an internal standard. The identity of the product as 2,6,7-trimethyl-2,6-octadiene was confirmed by comparison of the mass spectrum and the retention time to a known sample of the product synthesized independently.

We claim:

1. A compound of the formula

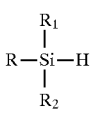

where R is a solid support comprising polystyrene; $R_1$ and $R_2$ are alkyl, substituted alkyl, or phenyl, and where $R_1$ and $R_2$ can be the same or different.

2. The compound of claim 1, where the polystyrene is cross-linked with divinyl benzene.

3. The compound of claim 1, where $R_1$ and $R_2$ are $C_1$–$C_4$ alkyl.

4. The compound of claim 3, where $R_1$ and $R_2$ are methyl.

5. A compound of the formula

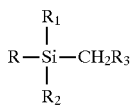

where R is a solid support comprising polystyrene; $R_1$ and $R_2$ are alkyl, unsubstituted alkyl, or phenyl, where $R_1$ and $R_2$ can be the same or different; and $R_3$ is alkyl, aromatic, or unsaturated alkyl, where $R_3$ can be substituted or unsubstituted.

6. The compound of claim 5, where the polystyrene is cross-linked with divinyl benzene.

7. The compound of claim 5, where $R_1$ and $R_2$ are methyl.

8. The compound of claim 5, where $R_3$ is unsaturated alkyl.

9. The compound of claim 8, where $R_3$ is allyl, dimethylallyl or geranyl.

10. A process for synthesizing a compound of the formula

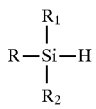

where R is a solid support comprising polystyrene and $R_1$ and $R_2$ can be the same or different and are alkyl, substituted alkyl or phenyl; comprising reacting a compound of the formula R—X, where X is bromine or iodine, with a lithium-containing compound to form a compound of the formula R—Li, and reacting the R—Li compound with a compound of the formula $HSiR_1R_2Cl$.

11. The process of claim 10, where $R_1$ and $R_2$ are methyl.

12. The process of claim 10, where the polystyrene is cross-linked with divinyl benzene.

13. A process for synthesizing a compound of the formula

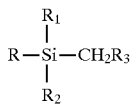

where R is a solid support comprising polystyrene, $R_1$ and $R_2$ can be the same or different and are alkyl, substituted alkyl, or phenyl; and $R_3$ is alkyl, aromatic or unsaturated alkyl, where $R_3$ can be substituted or unsubstituted; comprising (a) lithiating a compound of the formula

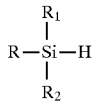

to form a lithium-containing compound of the formula

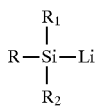

and (b) reacting said lithium containing compound with a compound of the formula $$R_3CH_2Z$$

where Z is a leaving group.

14. The process of claim 13, where $R_1$ and $R_2$ are methyl.

15. The process of claim 13, where Z is chlorine.

16. The process of claim 13, where $R_3$ is unsaturated alkyl.

17. The process of claim 15, where $R_3CH_2$ is allyl, dimethyl allyl, or geranyl.

18. A process for synthesizing a compound of the formula $R_3CH_2$, where $R_3$ is alkyl, aromatic, or unsaturated alkyl, and $R_3$ can be substituted or unsubstituted, comprising (a) lithiating a compound of the formula $$R-\underset{\underset{R_2}{|}}{\overset{\overset{R_1}{|}}{Si}}-H \qquad (I)$$

where R is a solid support comprising polystyrene, and $R_1$ and $R_2$ can be the same or different, and are alkyl, substituted alkyl or phenyl, to form a lithium-containing compound of the formula $$R-\underset{\underset{R_2}{|}}{\overset{\overset{R_1}{|}}{Si}}-Li \qquad (II)$$

(b) reacting said lithium containing compound with a compound of the formula $R_3CH_2Z$, where $R_3$ is alkyl, aromatic or unsaturated alkyl and can be substituted or unsubstituted, and Z is a leaving group, to form a compound of the formula $$R-\underset{\underset{R_2}{|}}{\overset{\overset{R_1}{|}}{Si}}-CH_2R_3 \qquad (III)$$

and (c) cleaving the compound of formula (III) at the Si—$CH_2$ bond.

19. The process of claim 18, where $R_3$ is unsaturated alkyl.

20. The process of claim 19, where $R_1$ and $R_2$ are methyl.

21. The process of claim 20, where Z is chlorine.

* * * * *